(12) United States Patent
Hebert et al.

(10) Patent No.: US 7,572,254 B2
(45) Date of Patent: Aug. 11, 2009

(54) APPARATUS AND METHODS FOR DIRECTIONAL DELIVERY OF LASER ENERGY

(75) Inventors: Chris J. Hebert, Lafayette, LA (US); Wade A. Bowe, Colorado Springs, CO (US); Timothy J. Wood, Monument, CO (US); Scott Tedder, San Antonio, TX (US)

(73) Assignee: The Spectranetics Corporation, Colorado Springs, CO (US)

( * ) Notice: Subject to any disclaimer, the term of this patent is extended or adjusted under 35 U.S.C. 154(b) by 568 days.

(21) Appl. No.: 11/228,845

(22) Filed: Sep. 16, 2005
(Under 37 CFR 1.47)

(65) Prior Publication Data

US 2006/0167442 A1 Jul. 27, 2006

Related U.S. Application Data

(60) Provisional application No. 60/611,191, filed on Sep. 17, 2004.

(51) Int. Cl.
*A61B 18/18* (2006.01)
(52) U.S. Cl. ............................. 606/15; 606/13; 606/14
(58) Field of Classification Search ................ 606/7
See application file for complete search history.

(56) References Cited

U.S. PATENT DOCUMENTS

| | | | |
|---|---|---|---|
| 5,026,366 A * | 6/1991 | Leckrone | 606/7 |
| 5,318,032 A * | 6/1994 | Lonsbury et al. | 600/435 |
| 5,425,355 A | 6/1995 | Kulick | |
| 5,755,714 A * | 5/1998 | Murphy-Chutorian | 606/15 |
| 5,792,118 A * | 8/1998 | Kurth et al. | 604/246 |
| 5,891,133 A * | 4/1999 | Murphy-Chutorian | 606/7 |
| 6,022,342 A * | 2/2000 | Mukherjee | 604/523 |
| 6,056,743 A * | 5/2000 | Ellis et al. | 606/15 |
| 2002/0103459 A1* | 8/2002 | Sparks et al. | 604/164.13 |
| 2005/0149176 A1* | 7/2005 | Heggestuen et al. | 623/1.46 |
| 2006/0094930 A1* | 5/2006 | Sparks et al. | 600/104 |

* cited by examiner

*Primary Examiner*—Henry M Johnson, III
*Assistant Examiner*—Lynsey Crandall
(74) *Attorney, Agent, or Firm*—Townsend and Townsend and Crew LLP

(57) ABSTRACT

In some embodiments, without limitation, the invention comprises a catheter having an elongated housing with a channel disposed therein. A laser delivery member is movable and at least partially disposed within the channel. A ramp is disposed within the housing at an angle to its central axis and proximate to its distal end. The ramp is adapted to move the distal end of the laser delivery member outwardly from the central axis of the housing. A guidewire biases the distal end of the laser delivery member generally inwardly toward the central axis of the housing. In some embodiments, without limitation, the offset of the central axis of the tip of the laser delivery member from the central axis of the housing is determined by adjusting the extent to which the laser delivery member travels on the ramp, and disposition of the laser delivery member on the guidewire maintains the offset tip substantially parallel to the central axis of the housing. Thus, in accordance with the invention, the distal end of the laser delivery member may be biased in a desired direction or offset, permitting ablation of an area larger than the area of the distal end of the catheter.

35 Claims, 6 Drawing Sheets

APPARATUS AND METHODS FOR DIRECTIONAL DELIVERY OF LASER ENERGY

CROSS-REFERENCE TO RELATED APPLICATIONS

This application claims the benefit of U.S. Provisional Application Ser. No. 60/611,191 filed Sep. 17, 2004, which is hereby incorporated by reference in its entirety.

TECHNICAL FIELD

The embodiments described herein are generally directed to improved apparatus and methods for the delivery of laser energy, including without limitation, to a laser delivery catheter.

BACKGROUND

Arteries are the primary blood vessels that are responsible for providing blood and oxygen to the heart muscle. Arterial disease occurs when arteries become narrowed or blocked by a buildup of plaque (as some examples, atherosclerotic plaque or other deposits). When the blockage is severe, the flow of blood and oxygen to the heart muscle is reduced, causing chest pain. Arterial blockage by clots formed in a human body may be relieved in a number of traditional ways. Drug therapy, including nitrates, beta-blockers, and peripheral vasodilatator drugs to dilate the arteries or thrombolytic drugs to dissolve the clot, can be effective. If drug treatment fails, angioplasty may be used to reform or remove the atherosclerotic plaque or other deposits in the artery.

Traditional balloon angioplasty is sometimes used to address the blockage by inserting a narrow, flexible tube having a balloon into an artery in the arm or leg. The blocked area in the artery can be stretched apart by passing the balloon to the desired treatment site and gently inflating it a certain degree. In the event drug therapy is ineffective or angioplasty is too risky (often introduction of a balloon in an occluded artery can cause portions of the atherosclerotic material to become dislodged which may cause a total blockage at a point downstream of the subject occlusion thereby requiring emergency procedures), the procedure known as excimer laser angioplasty may be indicated.

Excimer laser angioplasty procedure is similar in some respects to conventional coronary balloon angioplasty. A narrow, flexible tube, the laser catheter, is inserted into an artery in the arm or leg. The laser catheter contains one or more optical fibers, which can transmit laser energy. The laser catheter is then advanced inside the artery to the targeted obstruction at the desired treatment site. After the laser catheter has been positioned, the laser is energized to "remove" the obstruction.

In many procedures, the lesion is often engaged similar to conventional balloon angioplasty by crossing the blockage with a guidewire. The laser catheter's thin, flexible optical fibers facilitate the desired positioning and alignment of the catheter. Using the excimer laser, the clinician performs a controlled blockage removal by sending bursts of ultraviolet light through the catheter and against the blockage, a process called "ablation." The catheter is then slowly advanced through the blockage reopening the artery. If there are multiple blockages, the catheter is advanced to the next blockage site and the above step is repeated. When the indicated blockages appear to be cleared, the catheter is withdrawn.

However, due to the configuration of the optical fibers in most prior art laser catheters, the clinician is able to ablate only material that is typically directly in front of the distal end of the catheter. Thus, the debulked tissue area is limited to an area approximately the size of the optical fiber area at the distal end of the catheter. Typically, follow-up angioplasty is recommended.

Thus, it would be desirable to provide an apparatus and methods that could bias the distal end of the laser catheter in a desired direction to enable the clinician to ablate an area larger than the area of the distal end of the catheter. Furthermore, because plaque may be eccentric in a blood vessel and require directional control to adequately ablate the target area, it would be advantageous to provide an apparatus that is sufficiently flexible to travel and rotate around the target area so that the clinician may control the area to be ablated.

SUMMARY

In accordance with some embodiments, without limitation, the invention comprises a catheter having an elongated housing including a central axis between a first proximal end and a first distal end. The housing has a channel disposed between the first proximal end and the first distal end in communication with a cavity disposed proximate the first distal end. A laser delivery member is movable and at least partially disposed within the channel having a second proximal end and a second distal end. A ramp is disposed at an angle to the central axis and proximate the first distal end of the elongated housing within the cavity. The ramp is in communication with the channel and is adapted to move the second distal end of the laser delivery member outwardly from the central axis of the elongated member. A guidewire is in mechanical communication with both the laser delivery member and the elongated housing. The guidewire is adapted to bias the second distal end of the laser delivery member generally inwardly toward the central axis of the housing. In some embodiments, without limitation, the ramp is used to determine the offset of the central axis of the tip of the laser delivery member from the central axis of the housing, while keeping the axes substantially parallel, by adjusting the extent to which the laser delivery member travels on the ramp, and the disposition of the laser delivery member on the guidewire maintains the offset tip substantially parallel to the central axis of the housing. Methods of using same are also disclosed.

BRIEF DESCRIPTION OF THE DRAWINGS

The features and inventive aspects of the present invention will become more apparent upon reading the following detailed description, claims, and drawings, of which the following is a brief description:

DETAILED DESCRIPTION

Figure 1:
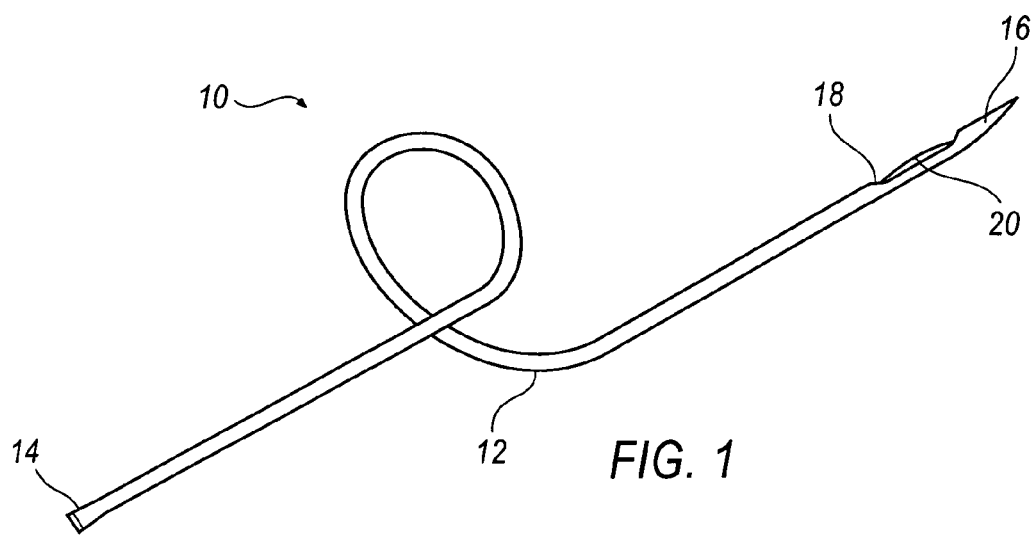
FIG. 1 is perspective elevated view of a catheter according to one embodiment.
Figures 2, 3:
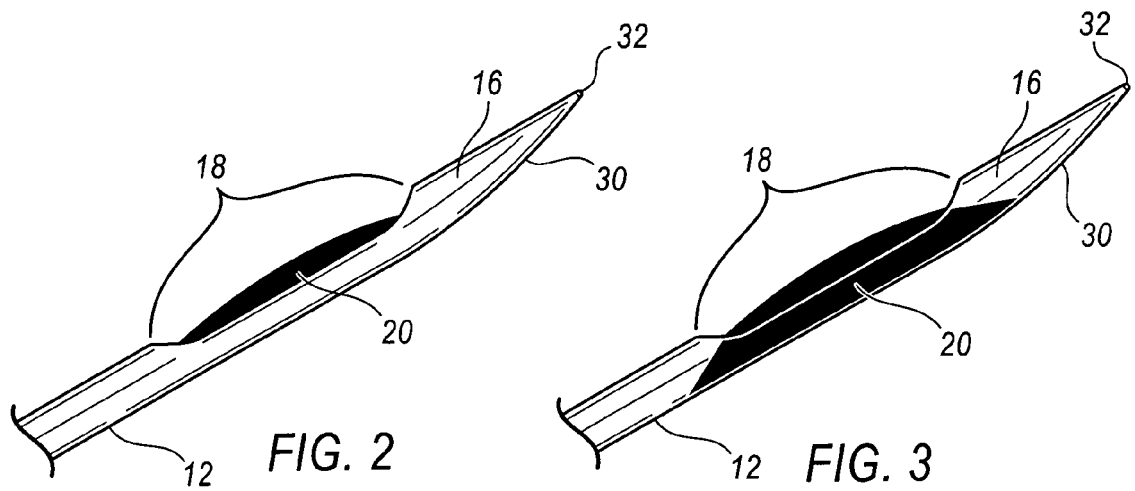
FIG. 2 is an exploded perspective view of a cavity of FIG. 1.
FIG. 3 is an exploded perspective view of FIG. 1 showing one embodiment of a ramp.
Figure 4:
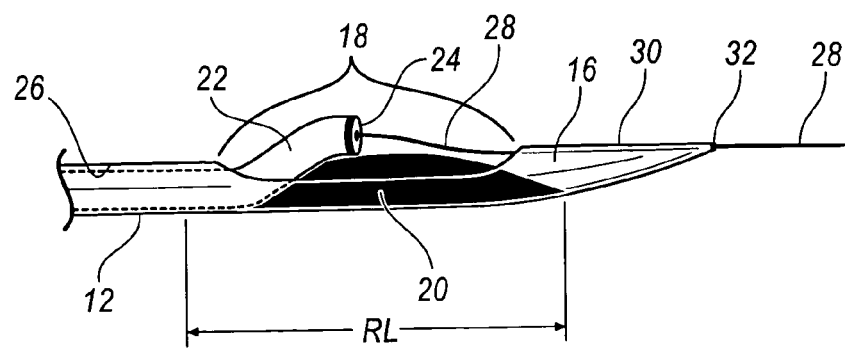
FIG. 4 is an exploded perspective view of FIG. 1 showing a ramp, a laser delivery member, and a guidewire.

Referring now to the drawings, illustrative embodiments are shown in detail. Although the drawings represent some embodiments, the drawings are not necessarily to scale and certain features may be exaggerated to better illustrate and explain an innovative aspect of an embodiment. Further, the embodiments described herein are not intended to be exhaustive or otherwise limit or restrict the embodiments of the invention to the precise form and configuration shown in the drawings and disclosed in the following detailed description.

Referring now to FIGS. 1-4, a catheter 10 is shown having an elongated housing 12. The elongated housing 12 includes a central axis between a first proximal end 14 and a first distal end 16. A cavity 18 is located proximate to the first distal end 16 of elongated housing 12 having a ramp 20 at an angle to the central axis of the housing 12. The angle of the ramp 20 may but need not be the same over the length of the ramp. In some preferred embodiments, without limiting the scope of the invention, the housing includes a tapering end 30 and a guide wire aperture 32 capable of accepting the guidewire 28. A laser delivery member 22 comprising one or more optical fibers capable of transmitting light energy is disposed within a channel 26 of the housing 12 having a second proximal end (not shown) and a second distal end 24 movable therein. In some embodiments, without limitation, the laser delivery member 22 may be in mechanical communication with a guidewire 28 as further discussed below.

The guidewire 28 is threaded through a needle (not shown) into the artery and the needle is removed. The guidewire is advanced to or near the treatment site and may be inserted at its distal end into or across the lesion to be treated, as desired. The guidewire 28 serves as a tracking guide for the housing 12 and laser delivery member 22 to run on. Guidewires for such uses are known in the art and may comprise those with diameters between about 0.010 and 0.06 inches, with 0.014 and 0.018 inches diameter being typical sizes for artery applications. The guidewires may have bendable tips of coiled wire or plastic and a more rigid shaft of tapered ground stainless steel or other suitable material for push and torque transmission. The housing 12 and laser delivery member 22 are introduced coaxially, either sequentially or simultaneously, onto the guidewire 28 and advanced to a target area as further discussed below.

In some embodiments, without limitation, the housing 12 is introduced onto the guidewire 28 that has been inserted into the patient, and the housing is advanced to or near the treatment site such that portions of the guidewire 28 are disposed at least initially within the guide wire aperture 32, tapering end 30, and channel 26 of the housing. The laser delivery member 22 is then introduced onto the guidewire 28 so disposed within the catheter 10. The laser delivery member 22 is then advanced along the guidewire 28 such that the distal end 24 of the laser delivery member 22 becomes supported by the ramp 20 and oriented within the cavity 18 at any angle between 1 degree and 90 degrees in relation to the central axis of the housing 12, as desired by the user. Laser energy is then applied to the treatment site according to methods and protocols known to those of ordinary skill in the art. In some embodiments, without limiting the scope of the invention, in conjunction with the application of laser energy, the position of the laser delivery member 22 may optionally be varied by the user by moving the member 22 proximally or distally in order to adjust the angle of disposition of its distal end 24. Optionally, the offset of the central axis of the tip of the laser delivery member 22 from the central axis of the housing 12 may be varied by adjusting the distance that the delivery member 22 travels on the ramp 20 while keeping the central axis of the tip substantially parallel to the central axis of the housing 12. In addition, the catheter 10 containing the laser delivery member 22 may optionally be rotated along its central axis during the laser treatment and thereby apply laser energy to areas of the treatment site within the arc of the rotation. Optionally, the guidewire 28 may be withdrawn before application of laser energy and after the laser delivery member 22 has been introduced via the guidewire 28 into the channel 26 of the housing 12.

The elongated housing 12 is an elongated structure having a lumen or channel 26 large enough to accommodate the laser delivery member 22 and guidewire 28. The channel 26 extends the entire length of the housing 12 from the first proximal end 14 to the first distal end 16. Optionally, in some embodiments, the channel 26 may extend only to the ramp 20. Various control mechanisms including electrical, optical, and mechanical control mechanisms may be employed with the housing 12 permitting the catheter to be specifically directed to a target area (not shown) within the blood vessel. One embodiment of the housing includes a tapering end 30 and a guide wire aperture 32 capable of accepting the guidewire 28. The housing 12 may be made from any rigid, semi-flexible, or flexible material including a combination thereof made from a material including metal, plastic, rubber, and the like. Round or flat metal ribbon wire may be embedded within the material, inserted through the cavity 18, or disposed at the first distal end 16 to add stability to the housing 12 at the first distal end 16. The length of the housing 12 may be varied as desired. The housing 12 may be one piece or have a plurality of sections including a support structure section at the first distal end 16 as discussed further below. The distal end 16 of the housing 12 may include a non-traumatic polymer tip separate or integrated into the housing 12. This allows the forces seen in bending to be dissipated throughout the structure, reducing stress risers that could cause failure. The housing 12 may also include at least one wire disposed within the channel 26 to add robustness to the housing 12. The channel 26 is in communication with cavity 18 and wire aperture 32. The channel 26 is open to the exterior of the housing 12 through the cavity 18.

The ramp 20 is disposed within cavity 18 and is configured to project the laser delivery member 22 outwardly at various determinable angles. Optionally, the ramp 20 is used to determine the offset of the central axis of the tip of the laser delivery member 22 from the central axis of the housing 20, while keeping the axes substantially parallel, by adjusting the extent to which the laser delivery member 22 travels on the ramp 20. In some embodiments without limitation, the disposition of the laser delivery member 22 on the guidewire 28 maintains the offset tip substantially parallel to the central axis of the housing 12. In some embodiments, without limitation, the angle of lateral deviation of the ramp 20 from central axis of the housing 12 will vary in range as desired from one (1) degree to ninety (90) degrees, more usually in the range from thirty (30) degrees to sixty-five (65) degrees. By employing ramp 20 having different exit angles from the associated channel 26, different angles and/or offsets may be selected for treating a target area after the catheter 10 has been located within a patient. In some embodiments, without limitation, the ramp 20 may be adjustable, as one example only, by inflation of a balloon, and/or the ramp 20 may be slidable to allow varying degrees of offset.

The ramp 20 may be a built-up feature within the channel 26 of the housing 12 and may be located anywhere along the longitudinal length of the housing 12, but preferably at or within about 3 cm from the first distal end 16 of the housing 12. The ramp 20 may be formed or fused to the internal wall of the housing 12 and made from metal, plastic, rubber, and the like. In one embodiment, the ramp length (RL) is generally 1 cm. However, the ramp length (RL) may also be varied.

The first distal end 16 of the housing 12 may be formed from plastic, metal, or any combination thereof. When metal is used, materials must be selected to provide appropriate flexibility without producing failure since the cavity 18 tends to reduce the structural integrity of some portions of the housing 12. Thus, in some embodiments, the first distal end 16 comprises a shape memory alloy, as one example only, nickel-titanium alloy. In other embodiments, without limitation, the first distal end 16 may comprise a stent-like structure proximal, distal, within, or a combination of such proximate the cavity 18. The stent-like structure may be made from at least one of stainless steel, cobalt-chromium, nickel titanium, and the like.

Figure 5:
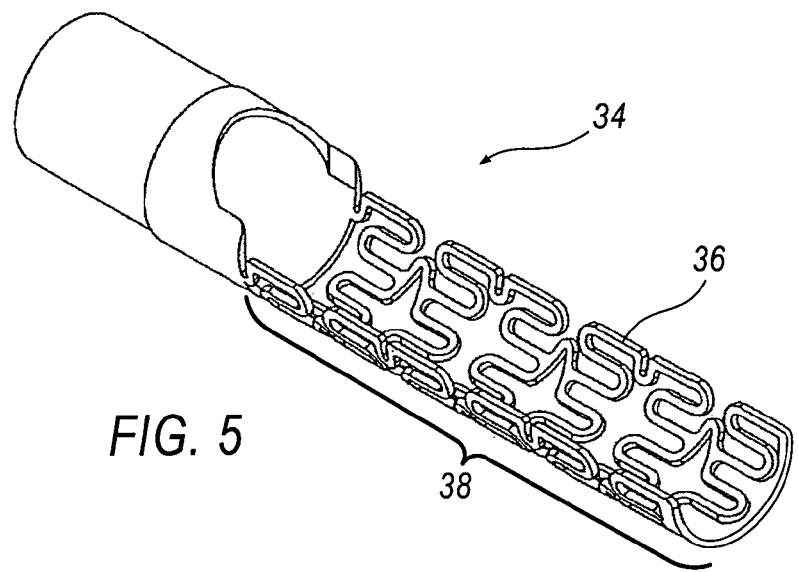
FIG. 5 is a perspective elevated view of a first embodiment of a support structure.
Figure 6:
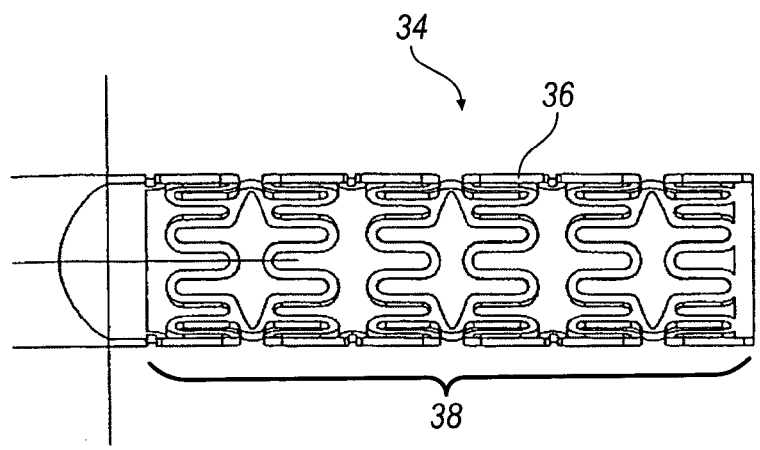
FIG. 6 is a top plan view of FIG. 5.
Figure 7:
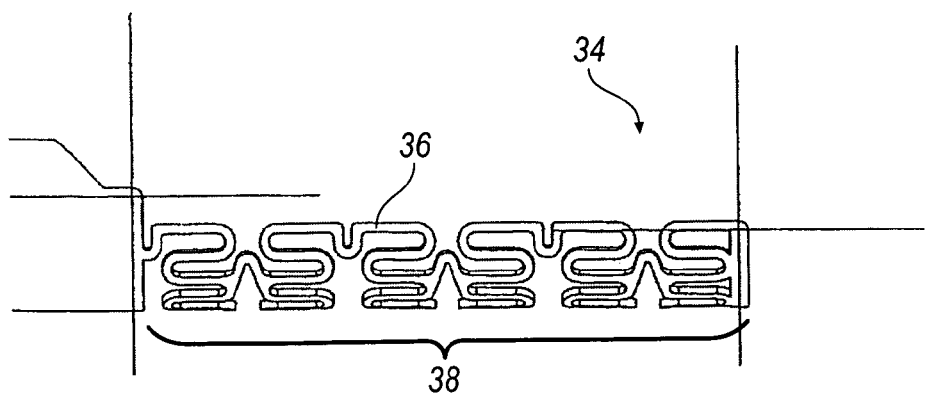
FIG. 7 is a side plan view of FIG. 5.

An alternative embodiment of the housing 12 comprises having at least one section at the first distal end 16. A first embodiment of a support structure is support member 34 as shown in FIGS. 5-7. The support member 34 may be used to support the first distal end 16 while providing flexibility without producing failure. The first distal end 16 of the housing 12 may otherwise experience limited torsional and bending strength of the area around the cavity 18 specifically traversing bends having a radius of about 0.75 inches. The support member 34 assists in withstanding the torsional and bending forces when traversing bends of about 0.75 inches, while maintaining aspects of both integrity and functionality. In some embodiments, without limitation, support member 34 reinforces the area around the cavity 18 at the first distal end 16 with struts 36 forming a stent-like pattern 38. Support member 34 is formed from metal, plastic, or combinations thereof, and is at least partially axially disposed around the wall of the first distal end 16 of the housing 12. The housing 12 may be one longitudinal piece or have a plurality of sections including the support structure as described above disposed at the first distal end 16 of the housing 12. Other embodiments of the support structure include a marker band proximate the first distal end 16 of the housing 12 and radiopaque markers at various intervals along the ramp 20 to demarcate acceptable ramp 20 positions for the catheter 10. As one example only, a user may place a catheter at a first mark on the ramp to increase the offset for ablation to 1 mm. A second mark might equal a 1.5 mm offset. This way the support structure may be used progressively, as one example only, as a progressive atherectomy tool. Additional embodiments having generally similar benefits may also be used, as further discussed below.

Figure 8:
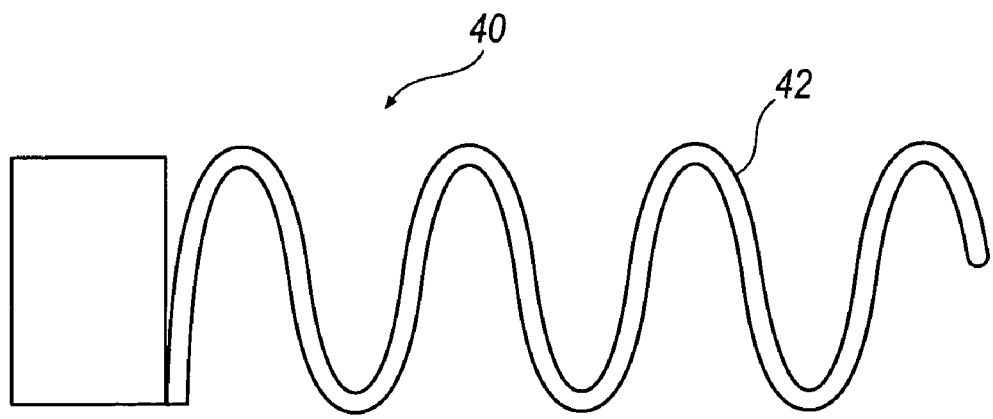
FIG. 8 is a top plan view of a second embodiment of a support structure.
Figure 9:
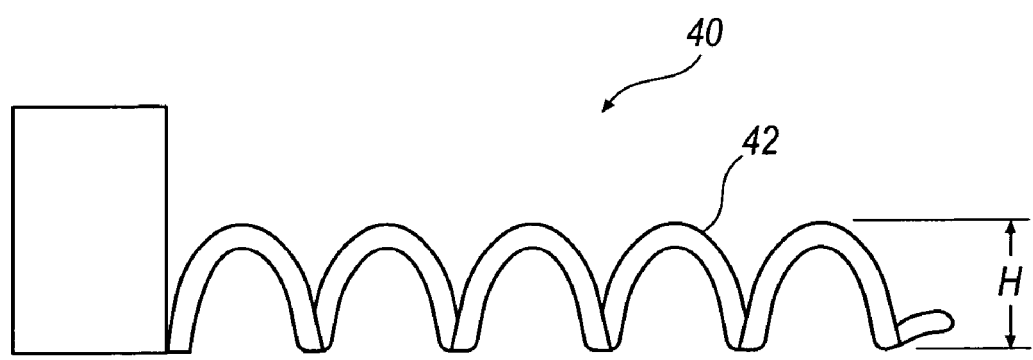
FIG. 9 is a side plan view of FIG. 8.

Referring to FIGS. 8 and 9, a second embodiment of a support structure is shown as second support member 40 having a spring-like geometry 42. The support member 40 may be used to support the first distal end 16 while providing flexibility without producing failure. The second support member 40 acts as a backbone for the first distal end 16 of the housing 12. The spring-like geometry 42 permits flexing without causing failure. The height H of the spring-like geometry 42 may be of any height but is preferably below the centerline of the second support member 40. The ramp 20 may be molded over the spring like geometry 42 including having a top coat (not shown).

Figure 10:
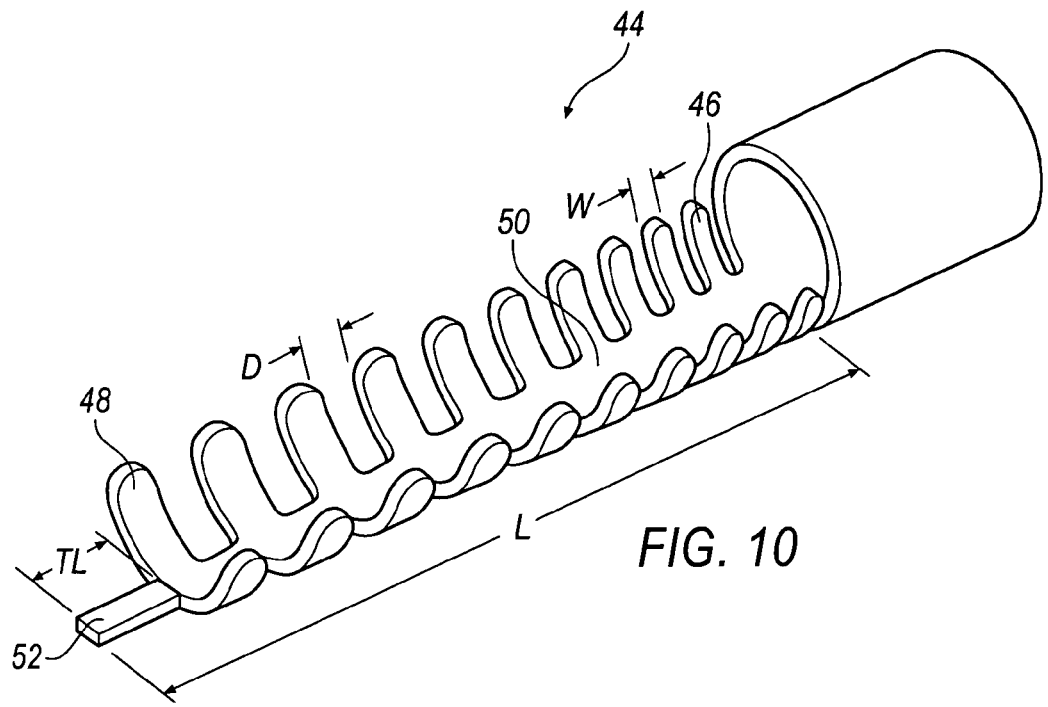
FIG. 10 is a perspective elevated view of a third embodiment of a support structure.
Figure 11:
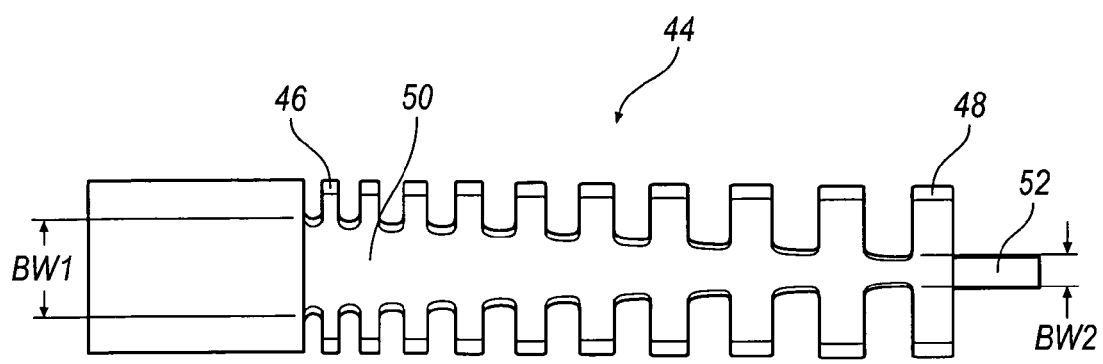
FIG. 11 is a top plan view of FIG. 10.

Referring to FIGS. 10 and 11, a third embodiment of a support structure is shown as a third support member 44. The support member 44 may be used to support the first distal end 16 while providing flexibility without producing failure. The third support member 44 provides variable stiffness along the length of the member 44. Member 44 is the most rigid at rib 46 and most flexible at rib 48. This flexibility is accomplished by having the ribs increase in width W and distance D in addition to decreasing the side of a beam 50 as shown in FIG. 11. Beam 50 tapers from a first wide beam width BW1 to a narrower beam width BW2. A tip 52 having a tip length TL disposed at the distal end support member 44 functions to provide support for the first distal end 16 of the housing 12 while allowing additional flexibility. The ramp 20 may be molded over the spring-like geometry 42 including having a top coat (not shown). The support member length L may be varied depending on user requirements including varying the tip length TL.

Figure 12:
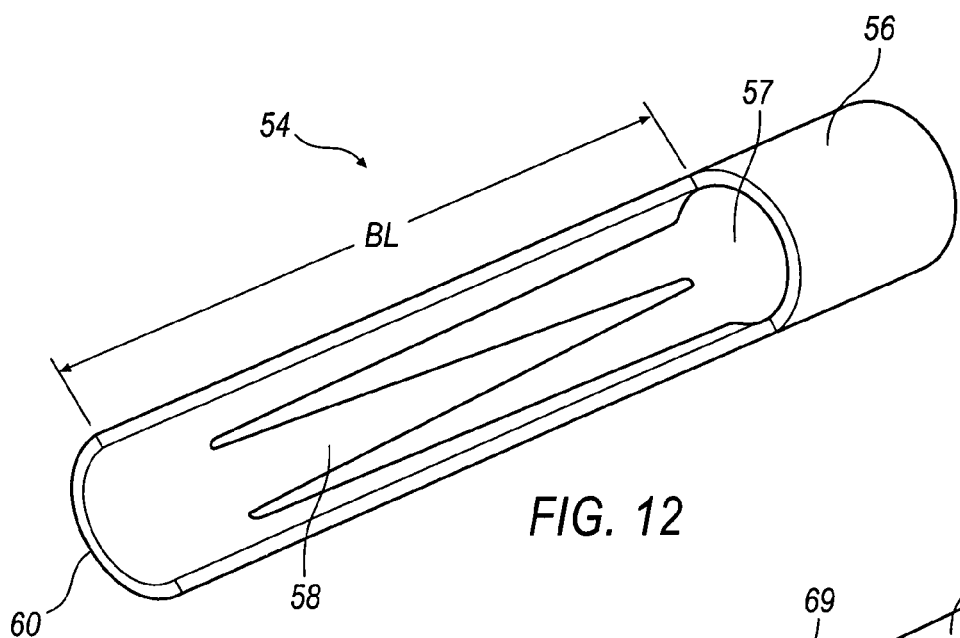
FIG. 12 is a perspective elevated view of a fourth embodiment of a support structure.

FIG. 12 shows a fourth embodiment of a support structure as fourth support member 54 disposed at the first distal end 16 of the housing 12. The support member 54 may be used to support the first distal end 16 while providing flexibility without producing failure. Support member 54 includes a rigid body 56 and a variably rigid base 58 extending from the body 56. Body 56 includes an aperture 57 in communication with channel 26. The base 58 may be elastomeric having the greatest flexibility at distal end 60. The ramp 20 may be molded over the base 58 including having a top coat (not shown). The support member base length BL may be varied according to user requirements.

Figure 13:
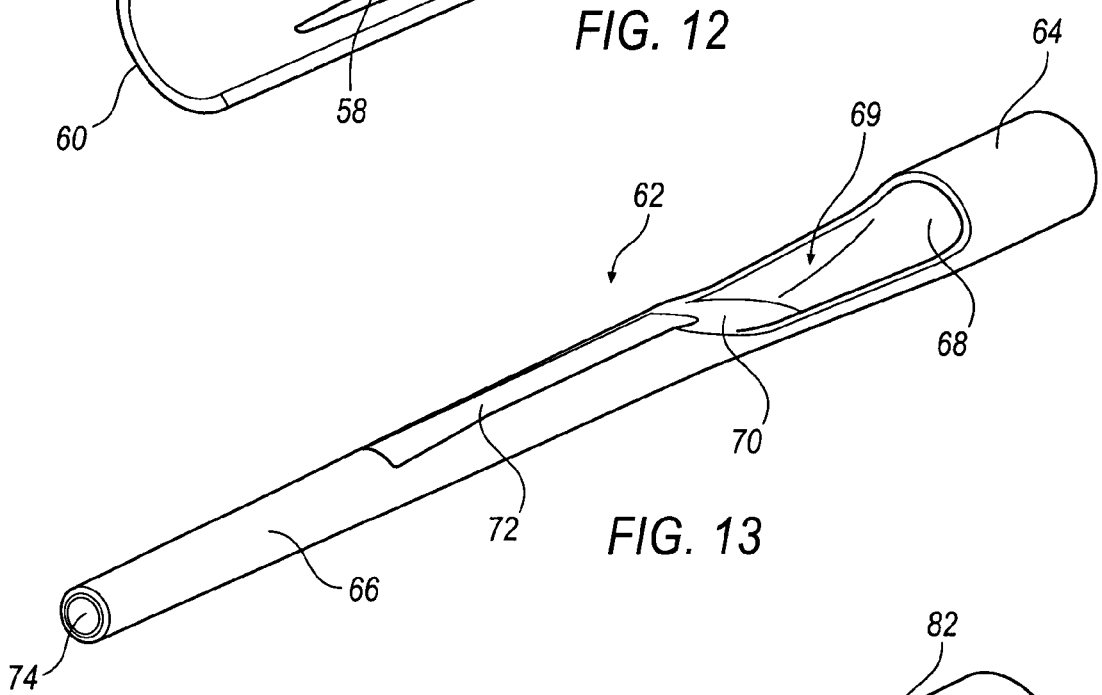
FIG. 13 is a perspective elevated view of a fifth embodiment of a support structure.

FIG. 13 shows a fifth embodiment of a support structure as fifth support member 62. The support member 62 includes a rigid body 64 having a flexible tapered nose portion 66. At least the nose portion 66 may be comprised of elastomeric material, as one example only, Rebax 55D available from Arkema. The body 64 is configured to communicate with the first distal end 16 of the housing 12. An aperture 68 is disposed within body 64 in communication with channel 26 of the housing 12 and is configured to accommodate both the laser delivery member 22 and guidewire 28. Aperture 68 is also in communication with the nose widow 69. The nose window 69 of the nose portion 66 includes a nose ramp 70 configured to project the laser delivery member 22 outwardly at various predetermined angles. Optionally, the ramp 20 is used to determine the offset of the central axis of the tip of the laser delivery member 22 from the central axis of the housing 20, while keeping the axes substantially parallel, by adjusting the extent to which the laser delivery member 22 travels on the ramp 20. In some embodiments without limitation, the disposition of the laser delivery member 22 on the guidewire 28 maintains the offset tip substantially parallel to the central axis of the housing 12. Usually, the angle of lateral deviation of the ramp 20 from the housing 12 will vary in range as desired from one (1) degree to ninety (90) degrees, more usually in the range from thirty (30) degrees to sixty-five (65) degrees. The nose portion also includes a nose channel 72 and a nose guidewire aperture 74. The guidewire 28 disposed within and in mechanical communication the laser delivery member 22 extends outwardly from the second distal end 24 of the laser delivery member 22 and is guided through the nose channel 72 and extending out the guidewire aperture 74. Both the nose channel 72 and guidewire aperture 74 provide securement for the guidewire 28 so that the guidewire 28 may properly bias the second distal end 24 of the laser delivery member 22 generally inwardly toward the central axis of the body 64.

Figure 14:
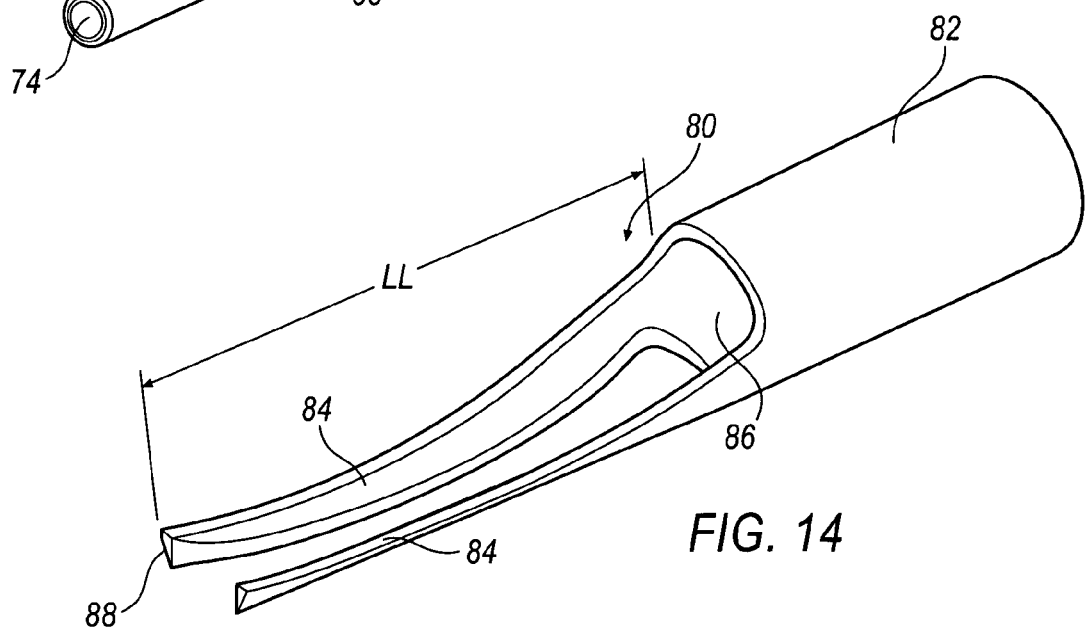
FIG. 14 is a perspective elevated view of a sixth embodiment of a support structure.

FIG. 14 shows a sixth embodiment of a support structure as sixth support member 80. The support member 80 may be used to support the first distal end 16 while providing flexibility without producing failure. Support member 80 includes a rigid body 82 and at least two variably rigid legs 84 extending from the body 82. Body 82 includes an aperture 86 in communication with the channel 26. The body 82 may be elastomeric having the greatest flexibility at distal end 88. The legs 84 may be of any shape extending from the body 82. The ramp 20 may be molded over the legs 84 including having a top coat (not shown). The support member leg length LL may be varied depending on user requirements.

Figure 15:
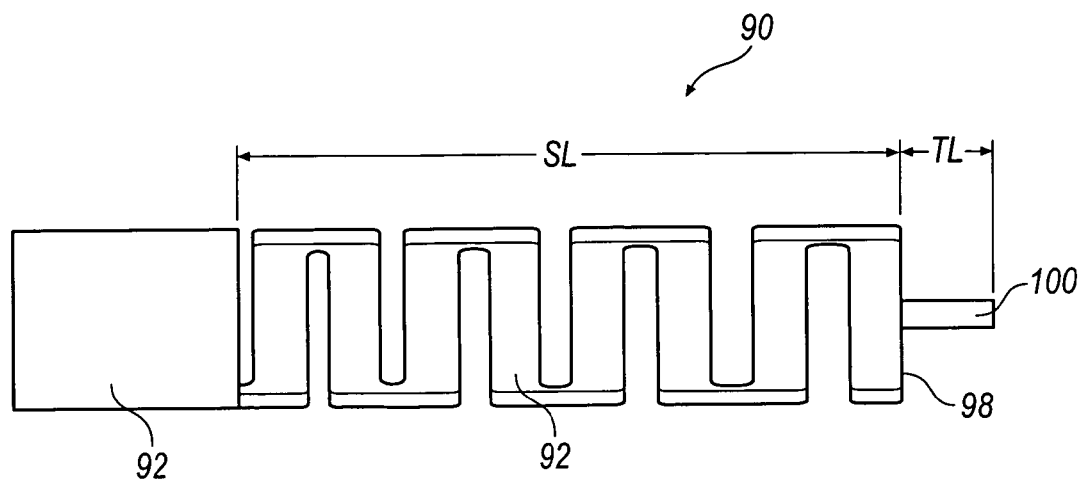
FIG. 15 is a top plan view of a seventh embodiment of a support structure.
Figure 16:
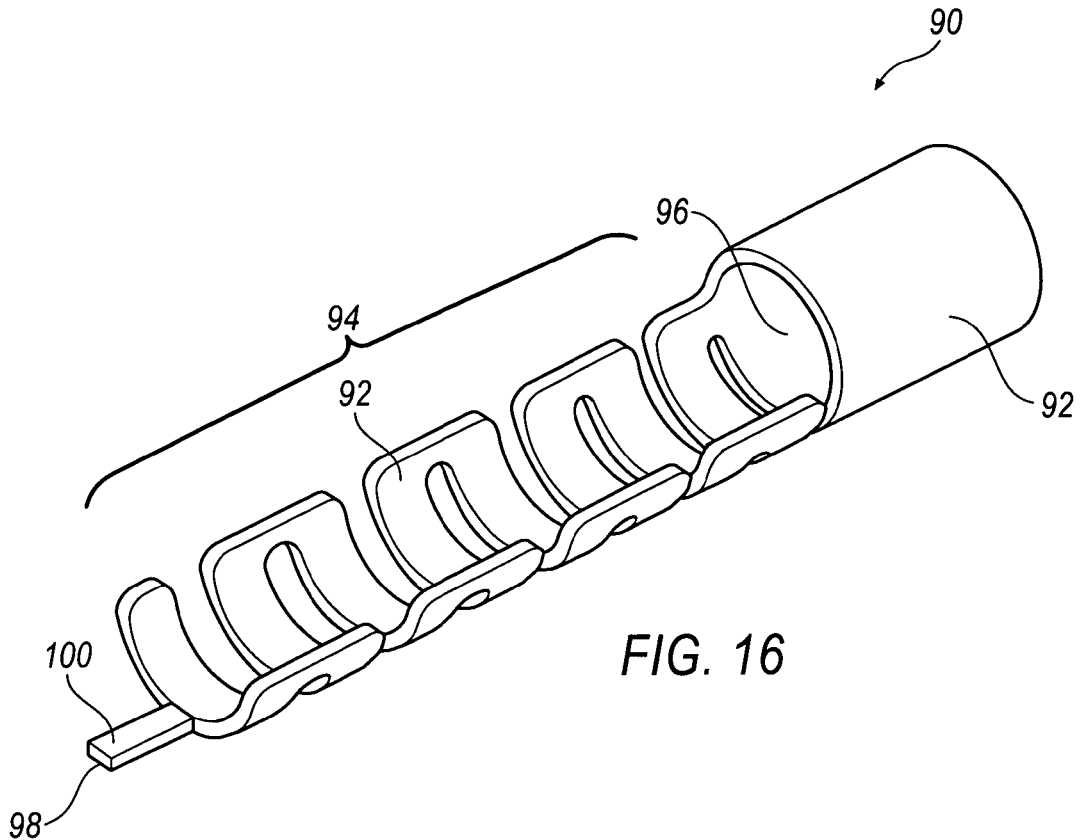
FIG. 16 is a perspective elevated view of FIG. 15.

FIGS. 15 and 16 show a seventh embodiment of a support structure as seventh support member 90. The support member 90 may be used to support the first distal end 16 while providing flexibility without producing failure. The first distal end 16 of the housing 12 may otherwise experience limited torsional and bending strength of the area around the cavity 18 specifically traversing bends having a radius of about 0.75 inches. The support member 90 assists in withstanding the torsional and bending forces when traversing bends of about 0.75 inches while maintaining both integrity and functionality. Support member 90 reinforces the area around the cavity 18 at the first distal end 16 with a braid 92 forming a stent-like pattern 94. Support member 90 is formed from metal or plastic and is at least partially axially disposed around the wall of the first distal end 16 of the housing 12. The housing 12 may be one longitudinal piece or have a plurality of sections including the support structure as described above disposed at the first distal end 16 of the housing 12. Support member 90 includes a rigid body 92 and a variably rigid base 94 forming the stent-like pattern 94 extending from the body 92. Body 92 includes an aperture 96 in communication with channel 26. The base 94 may be elastomeric having the greatest flexibility at distal end 98. A tip 100 having a tip length TL disposed at the distal end support member 90 functions to provide support for the first distal end 16 of the housing 12 while allowing additional flexibility. The ramp 20 may be molded over the base 94 including having a top coat (not shown). The support member stent-like length SL may be varied depending on user requirements.

In operation, once the guidewire 28 is in place, or as it is being positioned, the housing 12 is inserted. This housing 12 has a central channel 26, which may include the laser delivery member 22 and guidewire 28. The housing 12 and the laser delivery member 22 are advanced through the guidewire into the desired target area. Therefore, the guidewire 28 is in mechanical communication with both the laser delivery member 22 and the elongated housing 12. However, the housing 12 may be advanced prior to inserting the laser delivery member 22. As the laser delivery member 22 approaches the ramp 20, it is biased in an outwardly direction through the cavity 18. The further the laser delivery member 22 is advanced, the more it projects outwardly from the cavity 18 at the first distal end 16 of the housing 12. In some embodiments, without limitation, the guidewire 28 disposed within the laser delivery member 22 biases the second distal end 24 of the laser delivery member 22 inwardly providing a travel path and forcing the second distal end 24 to face forward along the guidewire 28 and generally parallel to the centerline of the housing 12. Otherwise, the second distal end 24 of the laser delivery member 22 would continue along the ramp 20 further projecting away from the centerline of the housing 12 and would not be "attacking" the target area in front of the catheter 10 as desired.

The preceding description has been presented only to illustrate and describe exemplary embodiments of the methods and systems of the present invention. It is not intended to be exhaustive or to limit the invention to any precise form disclosed. It will be understood by those skilled in the art that various changes may be made and equivalents may be substituted for elements thereof without departing from the scope of the invention. In addition, many modifications may be made to adapt a particular situation or material to the teachings of the invention without departing from the essential scope. Therefore, it is intended that the invention not be limited to the particular embodiment disclosed as the best mode contemplated for carrying out this invention, but that the invention will include all embodiments falling within the scope of the claims. The invention may be practiced otherwise than is specifically explained and illustrated without departing from its spirit or scope.

What is claimed is:

1. A catheter comprising:
an elongated housing having a central axis between a first proximal end and a first distal end, said housing having a channel disposed at least part way between said first proximal end and said first distal end, the elongated housing further including a tip at the first distal end, the tip having a first guidewire lumen;
a laser delivery member having a second proximal end and a second distal end and comprising at least one optical fiber, said laser member being at least partially disposed within said channel and movable therein, wherein the laser delivery member further includes a second guidewire lumen;
a cavity being disposed proximate said first distal end of said elongated housing and in communication with said channel;
a ramp proximate said first distal end of said elongated housing, said ramp being in communication with said channel and having an inclining proximal section and an apex section, said ramp adapted to move said second distal end of said laser delivery member laterally away from said central axis of said elongated member when the distal end of the laser delivery member is on the ramp; and
a guidewire extending through the second guidewire lumen of the laser delivery member, over the ramp and through the first guidewire lumen at the tip of the elongated housing, said guidewire being adapted to position said second distal end of said laser delivery member laterally away from and generally parallel to said central axis as the distal end of the laser delivery member is at or beyond the apex section of the ramp.

2. The catheter of claim 1, wherein said elongated housing is formed from a flexible material.

3. The catheter of claim 2, wherein said flexible material is sufficiently flexible to permit said housing to travel contralaterally within the vasculature of a mammal.

4. The catheter of claim 1, wherein said elongated housing includes a braided pattern along at least a portion of said housing.

5. The catheter of claim 1, wherein said elongated hosing includes a braided pattern along at least one half of a length of said housing.

6. The catheter of claim 1, wherein said elongated housing includes a round or flat metal ribbon wire embedded within said housing.

7. The catheter of claim 1, wherein said elongated housing includes a wire braid disposed proximate said first distal end.

8. The catheter of claim 1, wherein said elongated housing includes at least one wire disposed within said housing.

9. The catheter of claim 1, wherein said elongated housing includes a polymer tip disposed at said first distal end separate from or integrated into said housing.

10. The catheter of claim 1, wherein said elongated housing includes a stent-like structure disposed proximate at least one of said distal end, said proximal end, and therebetween.

11. The catheter of claim 10, wherein said stent-like structure is formed from one of stainless steel, cobalt-chromium, and nickel titanium or any combination thereof.

12. The catheter of claim 1, wherein said ramp is inflatable.

13. The catheter of claim 1, wherein said ramp is formed into an internal wall of said housing.

14. The catheter of claim 1, wherein said ramp is formed from one of a metal, plastic, and rubber.

15. The catheter of claim 1, wherein said ramp includes a marker band disposed along said ramp.

16. The catheter of claim 1, wherein said ramp includes at least one radiopaque marker disposed at a predetermined location along a longitudinal length of said ramp.

17. The catheter of claim 1, further comprising a support structure disposed at said first distal end of said housing.

18. The catheter of claim 17, wherein said support structure is integrated with said housing proximate said first distal end.

19. The catheter of claim 17, wherein said support structure includes an aperture in communication with said channel.

20. The catheter of claim 17, wherein said support structure includes a stent-like or coiled form.

21. The catheter of claim 17, wherein said support structure is progressively more flexible from a support structure proximal end to a support structure distal end.

22. The catheter of claim 17, wherein said support structure includes a surface comprising at least a portion having a stent-like pattern.

23. The catheter of claim 17, wherein said support structure includes said ramp molded into a surface of said support structure.

24. The catheter of claim 17, wherein said support structure supports said first distal end of said housing.

25. A catheter support structure comprising:
a housing having a proximal end, a distal end, a central axis, a proximal lumen, a distal lumen, and an aperture disposed at least partially within said housing so as to be between the proximal lumen and the distal lumen, wherein the proximal lumen and the distal lumen are adapted to hold a guidewire;
a ramp having an inclining proximal section and an apex section, said ramp being positioned between the proximal lumen and the distal lumen such that the apex is positioned laterally away from the proximal lumen and the distal lumen, the ramp being in communication with said aperture and adapted to move a distal end of a laser delivery member laterally away from said central axis after passing through the proximal lumen over the guidewire, and to position the distal end of the laser delivery member laterally away from and generally parallel to the central axis as the distal end of the laser delivery member is at or beyond the apex section of the ramp.

26. The catheter support structure of claim 25, wherein said ramp is molded into a surface of said housing.

27. The catheter support structure of claim 25, wherein said ramp is inflatable.

28. The catheter support structure of claim 25, wherein said ramp is formed into an internal wall of said housing.

29. The catheter support structure of claim 25, wherein said ramp is formed from one of a metal, plastic, and rubber, or any combination thereof.

30. The catheter support structure of claim 25, wherein said ramp includes a marker band disposed along said ramp.

31. The catheter support structure of claim 25, wherein said ramp includes at least one radiopaque marker disposed at a predetermined location along a longitudinal length of said ramp.

32. The catheter support structure of claim 25, wherein the distal lumen is adapted to receive a guidewire, said guidewire being adapted to bias the distal end of said laser delivery member generally inwardly toward said central axis.

33. The catheter support structure of claim 25, wherein said catheter support structure is integrated with a catheter housing.

34. The catheter support structure of claim 25, further comprising at least one flexible structure disposed proximate said distal end of said housing having a proximal end and a distal end, said at least one flexible structure is increasingly flexible from said proximal end to said distal end, and wherein said at least one flexible structure includes a stent-like or coiled form.

35. A catheter system, comprising:
a catheter sheath comprising a sheath body having a proximal end, a distal end, a proximal lumen, a distal lumen, a ramp disposed between the proximal lumen and the distal lumen, and an opening proximal to the ramp, wherein the ramp has an inclining proximal section and an apex section;
a laser delivery member having a proximal end and a distal end, wherein the laser delivery member is movable within the proximal lumen of the catheter sheath;
a guidewire adapted to extend through the proximal lumen and the distal lumen of the catheter sheath such that it passes over the ramp;
wherein the laser delivery member includes a guidewire lumen to permit the distal end of the laser delivery member to track along the guidewire as it moves along the ramp, with the guidewire adapted to position the distal end of the laser delivery member laterally away from and generally parallel to the central axis as the distal end of the laser delivery member is at or beyond the apex of the ramp.

* * * * *

UNITED STATES PATENT AND TRADEMARK OFFICE
CERTIFICATE OF CORRECTION

PATENT NO. : 7,572,254 B2  Page 1 of 1
APPLICATION NO. : 11/228845
DATED : August 11, 2009
INVENTOR(S) : Hebert et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 897 days.

Signed and Sealed this

Seventh Day of September, 2010

David J. Kappos
*Director of the United States Patent and Trademark Office*